United States Patent
Mullani

(12) United States Patent     (10) Patent No.: US 7,874,698 B2
Mullani     (45) Date of Patent: Jan. 25, 2011

(54) TRANSILLUMINATION HAVING ORANGE COLOR LIGHT

(76) Inventor: Nizar A. Mullani, 719 Santa Maria, Sugar Land, TX (US) 77478

( * ) Notice: Subject to any disclaimer, the term of this patent is extended or adjusted under 35 U.S.C. 154(b) by 554 days.

(21) Appl. No.: 11/227,206

(22) Filed: Sep. 16, 2005

(65) Prior Publication Data

US 2007/0063151 A1     Mar. 22, 2007

(51) Int. Cl.
*F21V 9/00* (2006.01)

(52) U.S. Cl. ............ 362/230; 362/572; 362/804

(58) Field of Classification Search ........... 362/230, 362/231, 804, 57; 600/476, 479
See application file for complete search history.

(56) References Cited

U.S. PATENT DOCUMENTS

| | | | |
|---|---|---|---|
| 4,281,645 A | 8/1981 | Jobsis | |
| 4,651,743 A | 3/1987 | Stoller | |
| 4,651,744 A | 3/1987 | Bristow | |
| 5,344,418 A * | 9/1994 | Ghaffari | ............... 606/9 |
| 5,921,921 A | 7/1999 | Potratz et al. | |
| 5,957,917 A | 9/1999 | Doiron et al. | |
| 6,668,187 B1 | 12/2003 | Porath | |
| 7,027,153 B2 * | 4/2006 | Mullani | ............... 356/369 |
| 2004/0201846 A1 | 10/2004 | Mullani | |
| 2004/0201980 A1 | 10/2004 | Fischer | |
| 2005/0168980 A1 | 8/2005 | Dryden | |

FOREIGN PATENT DOCUMENTS

| | | |
|---|---|---|
| EP | 1 281 370 | 2/2003 |
| WO | WO 2005/053773 | 6/2005 |

OTHER PUBLICATIONS

"Veinlite LED" [Online]—May 20, 2005; Retrieved from the Internet.

* cited by examiner

*Primary Examiner*—Thomas M Sember
(74) *Attorney, Agent, or Firm*—Welsh Flaxman & Gitler LLC

(57) ABSTRACT

The transillumination device has an orange light, in the range of 580-620 nm. Orange light has been found to be beneficial for superficial veins. Red light is used for deeper veins and darker skin. The transillumination device may have a single light source able to change colors. Two different light sources, each having a different color or different transillumination devices, each having a different color, may be used for diagnostic purposes.

7 Claims, 1 Drawing Sheet

TRANSILLUMINATION HAVING ORANGE COLOR LIGHT

BACKGROUND OF THE INVENTION

Transillumination entails shining of a light through a body cavity or organ for diagnostic purposes. Typically, transillumination is performed in a room where the lights have been dimmed or turned off to facilitate the viewing of the part being studied. A bright light is pointed at the cavity or organ and due to the slight translucence of the part under consideration, some of the light passes through the part or organ. This test is often performed on newborns or infants with hydrocephalus or males suspected of having hydrocele. In addition, for tests performed on breast tissue to detect lesions and/or cysts. In newborns, the test is used to transilluminate the chest cavity if pneumothorax is suspected. Only in newborns is transillumination of the chest possible. Transillumination is painless and quickly performed with inexpensive equipment.

Transilluminators use color to facilitate the viewing of the tissue organ under study. U.S. Pat. No. 4,651,743 (Stoller) discloses a transillumination device using red light. In addition, U.S. Pat. No. 5,957,917 (Doiron et al) discloses that red light is particularly useful for performing transillumination of tissue for diagnostic purposes.

It is an object of the invention to provide a transillumination device having different colored light for optimizing imaging.

It is another object of the invention to provide a transillumination device having an orange light.

It is another object of the invention to have a transillumination device with different colored lights for superficial veins and deeper veins.

These and other objects of the invention will become apparent to one of ordinary skill in the art after reviewing the disclosure of the invention.

SUMMARY OF THE INVENTION

The side transillumination device has an orange light, in the range of 580-620 nm. Orange light has been found to be beneficial for superficial veins. Red light is used for deeper veins and darker skin. The transillumination device may have a single light source able to change colors. Two different light sources, each having a different color or different transillumination devices, each having a different color, may be used for diagnostic purposes. The light source may be fiber optic or LED.

DETAILED DESCRIPTION OF THE INVENTION

Figure 1:
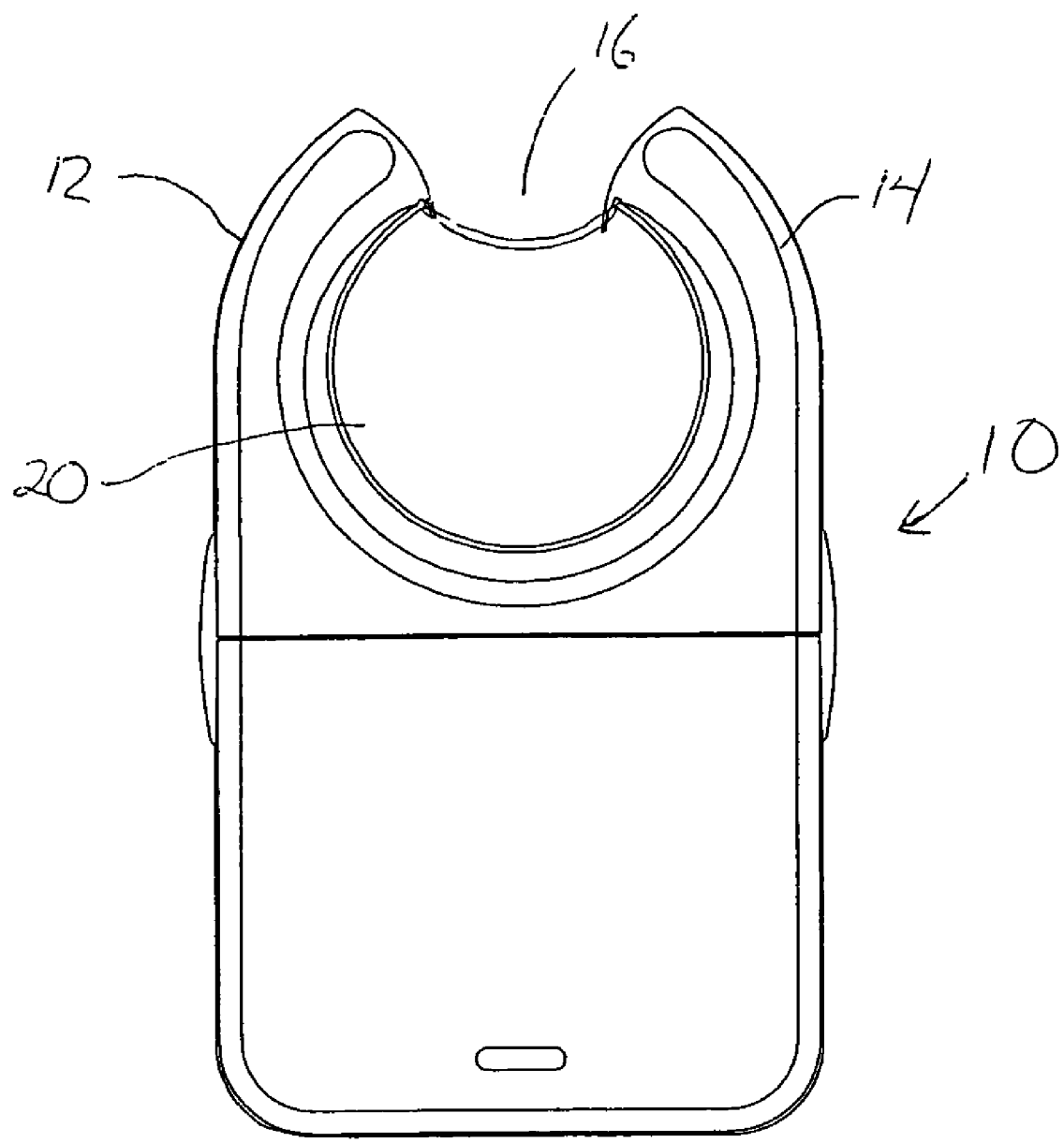
FIG. 1 is a bottom view of a transilluminator.

The transillumination device depicted in FIG. 1 has a housing 12 and a circular area of illumination 14 extending from the front edge and forming a viewing area 18. A light source 20, such as an LED, surrounds the viewing area. The housing contains a power source for the light source. The transilluminator is placed near the patient's skin for vein imaging. Other applications of transillumination devices are well known.

The use of an orange light, such as between 580 and 620 nm, allows enhanced imaging of superficial veins. Red light optimizes deeper veins and darker skin. The transillumination device may have a light source which can transmit both orange or red light. If necessary, two light sources, one of each color may be used in a single transillumination device. Alternatively, separate transillumination devices, one transmitting orange and one transmitting red, would enable the use of different colors for diagnostic testing.

While the invention has been described with reference to a preferred embodiment, variations and modifications would be apparent to one of ordinary skill in the art. Such variations and modifications are encompassed by the invention.

What is claimed is:

1. A side transillumination device comprising:
   a hand held medical device having a housing,
   a light emitting diode retained by said housing for vein imaging, said light emitting diode emitting an orange light from said side transillumination device, said orange light having a wavelength of only between 580 and 600 nm.

2. The side transillumination device of claim 1, further comprising
   a circular area of illumination extending from said housing,
   a viewing area formed between said circular area of illumination.

3. The side transillumination device of claim 1, further comprising
   a light source emitting a red light.

4. The side transillumination device in accordance with claim 1, further having a means for directing said orange light at an angle toward a patient's skin.

5. A method of vein imaging, comprising: providing a side transillumination device including a light emitting diode,
   placing said light emitting diode of said side transillumination device proximate to the patient's skin, said light emitting diode emitting an orange light having a wavelength of only between 580 and 600 nm;
   imaging a vein of the patient with said orange light for diagnostic purposes.

6. The method of claim 5, further comprising
   using a red light to view deeper veins.

7. The method in accordance with claim 5, further including the step of:
   directing said orange light at an angle toward the patient's skin.

* * * * *